United States Patent [19]
Iyer et al.

[11] Patent Number: 5,808,042
[45] Date of Patent: Sep. 15, 1998

[54] DETRITYLATION OF DMT-OLIGONUCLEOTIDES USING CATIONIC ION-EXCHANGE RESIN

[75] Inventors: Radhakrishnan P. Iyer; Zhiwei Jiang; Dong Yu, all of Shrewbury; Weitian Tan, Framingham; Sudhir Agrawal, Shrewsbury, all of Mass.

[73] Assignee: Hybridon, Inc., Cambridge, Mass.

[21] Appl. No.: 447,760

[22] Filed: May 23, 1995

[51] Int. Cl.[6] .............................. C07H 1/00; C07H 21/04; C07H 21/00
[52] U.S. Cl. ......................................... 536/25.31; 536/25.3
[58] Field of Search ................................. 536/25.3, 25.4, 536/25.31

[56] References Cited

PUBLICATIONS

Iyer et al. Synth. Commun. 25(22): 3611–3623, 1995. Mo. not available.
Agrawal and Iyer, *Curr. Op. In Biotech.* 6, 12–19 (1995).
Agrawal and Tang, *Antisense Res. And Dev.* 2, 261–266 (1992).
Agrawal, *Trends in Biotech.* 10, 152–158 (1992).
Bayever et al., *Antisense Res. Dev.* 3, 383–390 (1993).
Beaucage and Iyer, *Tetrahedron* 48, 2223–2311 (1992).
Beaucage, *Methods in Molecular Biology*, vol. 20, pp. 33–61 (1993).
Bonora, *Nucl. Acids Res.* 21, 1213–1217 (1993).
Cheng & Pettitt, *Prog. Biophys. Molec. Biol.* 58, 225–257 (1992).
Habus and Agrawal, *Nucl. Acids Res.* 22, 4350–4351 (1994).
Iyer et al., *Bioorg. Chem.* 23, 1 (1995).
Iyer et al., *Nucleosides & Nucleotides* 14(6), 1349–1357 (1995).
Kuijpers et al., *Nucl. Acids Res.* 18, 5197–5205 (1990).
Padmapriya et al., *Antisense Res. Dev.* 4, 185–199 (1994).
Ravikumar et al., *Tetrahedron* 50, 9255–9266 (1994).
Reddy et al., *Tetrahedron Lett.* 35, 4311–4314 (1994).
Stein and Cheng, *Science* 261, 1004–1012 (1993).
Theisen et al., *Nucleosides & Nucleotides* 12, 1033–1046 (1993).
Uhlmann and Peymann, *Chem Rev* 90, 543–584 (1990).
Zamecnik and Stephenson, *Proc. Natl. Acad. Sci. USA* 75, 280–284 (1978).
Zon and Stec, *Oligonucleotides and Analogues: A Practical Approach*, pp. 87–108 (F. Eckstein, Ed., 1991).
Zon, *Methods in Molecular Biology, vol. 20: Protocols for Oligonucleotides and Analogs*, 165–189 (S. Agrawal, Ed., Humana Press, 1993).

*Primary Examiner*—Gary L. Kunz
*Attorney, Agent, or Firm*—McDonnell Boehnen Hulbert & Berghoff

[57] ABSTRACT

The present invention comprises a method for quickly and efficiently detritylating oligonucleotides synthesized by standard chemical techniques. The method comprises contacting a 5'-DMT oligonucleotide with the $H^+$ form of a "DOWEX," "AMBERLYST" or "AMBERLITE" ion-exchange resin for about 10 minutes to about 2 hours. The method is particularly advantageous when used in large scale synthesis. The method is quicker than the standard acetic acid method and eliminates much of the post-detritylation processing associated with the acetic acid method.

8 Claims, 2 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:1:

C T C T C G C A C C    C A T C T C T C T C    C T T C T    2 5

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear (i i) MOLECULE TYPE: DNA (genomic)

(i i i) HYPOTHETICAL: NO (i v) ANTI-SENSE: YES (x i) SEQUENCE DESCRIPTION: SEQ ID NO:2:

CUCUCGCACC CATCTCTCTC CUUCU                                            2 5

( 2 ) INFORMATION FOR SEQ ID NO:3:

(i) SEQUENCE CHARACTERISTICS:
                (A) LENGTH: 25 base pairs
                (B) TYPE: nucleic acid
                (C) STRANDEDNESS: single
                (D) TOPOLOGY: linear (i i) MOLECULE TYPE: DNA (genomic)

(i i i) HYPOTHETICAL: NO (i v) ANTI-SENSE: YES (x i) SEQUENCE DESCRIPTION: SEQ ID NO:3:

AGCTGCTACT AGTAGCTCGA CATGT                                            2 5

DETRITYLATION OF DMT-OLIGONUCLEOTIDES USING CATIONIC ION-EXCHANGE RESIN

BACKGROUND OF THE INVENTION

1. Field of the Invention

This invention relates to methods for the chemical synthesis of oligonucleotides. In particular, this invention relates to methods of detritylating 5'-protected oligonucleotides.

2. Summary of the Related Art

Since Zamecnik and Stephenson, *Proc. Natl. Acad. Sci. USA* 75, 280–284 (1978), first demonstrated virus replication inhibition by synthetic oligonucleotides, there has been much interest in the use of antisense oligonucleotides as agents for the selective modulation of gene expression, both in vitro and in vivo. See, e.g., Agrawal, *Trends in Biotech.* 10, 152 (1992); Chang and Petit, *Prog. Biophys. Molec. Biol.* 58, 225 (1992); and Uhlmann and Peymann, *Chem. Rev.* 90, 543 (1990). Antisense oligonucleotides are constructed to be sufficiently complementary to a target nucleic acid to hybridize with the target under the conditions of interest and inhibit expression of the target. Antisense oligonucleotides may be designed to bind directly to DNA (the so-called "anti-gene" approach) or to viral RNA or mRNA. Id. Expression inhibition is believed to occur by interfering with transcription processing or translation, or inducement of target mRNA cleavage by RNase H.

Antisense oligonucleotides can be used as research tools in vitro to determine the biological function of genes and proteins. They provide an easily used alternative to the laborious method of gene mutation (e.g., deletion mutation) to selectively inhibit gene expression. The importance of this method is readily appreciated when one realizes that the elucidation of most known biological processes has been determined by deletion mutation.

Antisense oligonucleotides also may be used to treat a variety of pathogenic diseases by inhibiting gene expression of the pathogen in vivo. Oligonucleotide phosphorothioates (PS-oligos) have shown great therapeutic potential as antisense-mediated inhibitors of gene expression (Stein and Cheng, *Science* 261, 1004 (1993) and references therein) as evidenced by a number of ongoing clinical trials against AIDS and cancer. Agrawal and Tang, *Antisense Res. and Dev.* 2, 261 (1992) and references therein, and Bayever et al., *Antisense Res. Dev.* 3, 383 (1993). Various methods have been developed for the synthesis of oligonucleotides for such purposes. See generally, *Methods in Molecular Biology*, Vol. 20: *Protocols for Oligonucleotides and Analogs* pp. 165–189 (S. Agrawal, Ed., Humana Press, 1993); *Oligonucleotides and Analogues: A Practical Approach*, pp. 87–108 (F. Eckstein, Ed., 1991); and Uhlmann and Peyman, supra. The phosporamidite method (and variations thereon) is the most commonly used method of oligonucleotide synthesis. E.g., Beaucage in *Methods in Molecular Biology*, Vol. 20, supra, pp. 33–61; and Beaucage and Iyer, *Tetrahedron* 48, 2223 (1992).

The synthesis of oligonucleotides for antisense and diagnostic applications is now be routinely accomplished. Agrawal and Iyer, *Curr. Op. in Biotech.* 6, 12 (1995); and *Antisense Research and Applications* (Crooke and Lebleu, Eds., CRC Press, Boca Raton, 1993). Refinement of methodologies is still required, however, particularly when making a transition to large-scale synthesis (10 $\mu$mol to 1 mmol amd higher). Padmapriya et al., *Antisense Res. Dev.* 4, 185 (1994). Several modifications of the standard phosphoramidite methods have already been reported to facilitate the synthesis (Padmapriya et al., supra; Ravikumar et al., *Tetrahedron* 50, 9255 (1994); Theisen et al., *Nucleosides & Nucleotides* 12, 1033 (1993); Bonora, *Nucl. Acids Res.* 21, 1213 (1993); Habus and Agrawal, *Nucl. Acids Res.* 22, 43 (1994); and Iyer et al., *Nucleosides & Nucleotides* 14, ** (1995) (in press)) and isolation (Kuijpers et al. *Nucl. Acids Res.* 18, 5197 (1990); and Reddy et al., *Tetrahedron Lett.* 35, 4311 (1994)) of oligonucleotides.

In most instances, the isolation and purification of oligonucleotides are conducted with the 4,4'-dimethoxytrityl (DMT) 5' protecting group attached to the oligonucleotide. The DMT group serves as a hydrophobic handle to aid the separation of the desired oligonucleotides from truncated sequences (failure sequences) by reverse-phase HPLC. Following HPLC purification, the DMT group at the 5'-end of the oligonucleotide is usually removed by treatment with 80% acetic acid for one to two hours (depending on the scale of operation) and then desalted by using either molecular size exclusion, membrane dialysis, or SEP-PAK chromatography. Following the large-scale synthesis (1 mmol scale) and HPLC purification of certain modified oligonucleotides, however, detritylation of oligonucleotides is incomplete by routine treatment with 80% acetic acid. Thus, longer duration of treatment with acetic acid is necessary to complete the detritylation reaction. Unfortunately, prolonged exposure of the oligonucleotide to acetic acid results in some decomposition of the oligonucleotide (as evaluated by HPLC). Furthermore, when acetic acid is used for detritylation, it is necessary to strip the oligonucleotide free from released trityl alcohol by extraction of the oligonucleotide concentrate with ethyl acetate before further processing can be done. Sometimes during the extraction procedure there is incomplete phase separation between the organic and aqueous layers, resulting in some loss of the expensive oligonucleotide. Accordingly, improved methods of detritylation are needed. The technical problem to be solved is the detritylation of chemically synthesized oligonucleotides (particularly on large scale) without substantial loss of the oligonucleotide product.

SUMMARY OF THE INVENTION

The present invention provides a new method of detritylating chemically synthesized oligonucleotides. The method comprises passing 5'-DMT-oligonucleotides ("DMT-on") through the $H^+$ form of a "DOWEX" "AMBERLYST" or "AMBERLITE" resin. Other $H^+$ resins having similar characteristics to these resins are also suitable for use in the present invention. Detritylation is observed in less than 2 hours and most frequently in only 10 minutes. The method is advantageously used for detritylation of oligonucleotides following large scale synthesis.

The method of the invention offers several advantages over prior art methods: (a) it is easier and more convenient to use that the acetic acid method; (b) detritylation can be accomplished in much less time—10 minutes for the present invention versus 2 hours with acetic acid; (c) the extractive processing is eliminated because the DMT species released upon deprotection is retained by the resin and therefore does not contaminate the oligonucleotide; (d) there is less processing loss and significantly reduced processing time because of the elimination of the extractive processing; (e) no side reactions (e.g., depurination) is observed if the duration of detritylation reaction is restricted to 2 hours or less; and (f) the resin can be re-used after regeneration, further added to the cost savings.

The foregoing merely summarizes certain aspects of the present invention and is not intended, nor should it be construed, to limit the invention in any way. All patents and publications recited herein establish the state of the art and are hereby incorporated by reference in their entirety.

DETAILED DESCRIPTION OF THE PREFERRED EMBODIMENTS

Figure 1A:
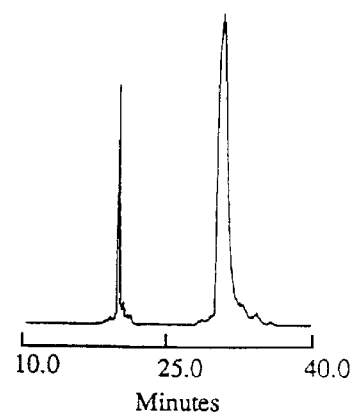
FIGS. 1A–F display HPLC profiles after detritylation of SEQ ID NO 3 (except Panel A, which is the profile of DMT-on SEQ ID NO 3) under various conditions. The inserts show the peaks on an expanded scale.
Figure 1B:
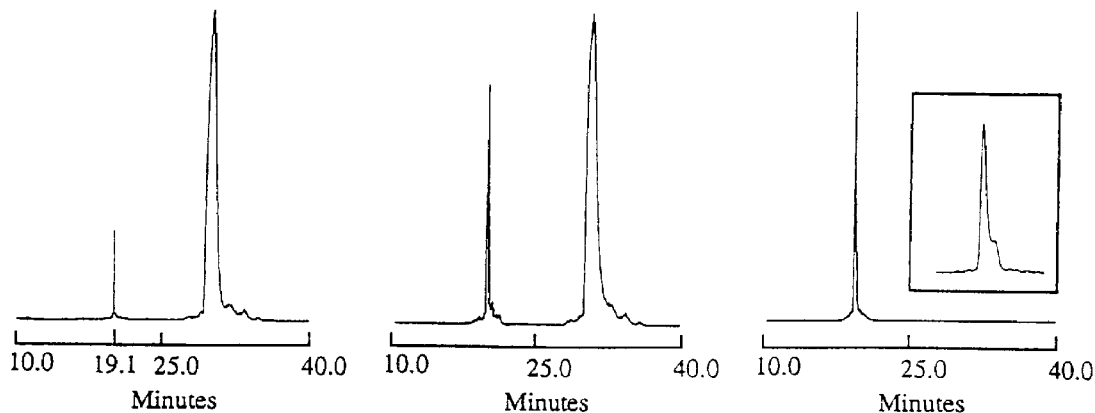
Figure 1C:
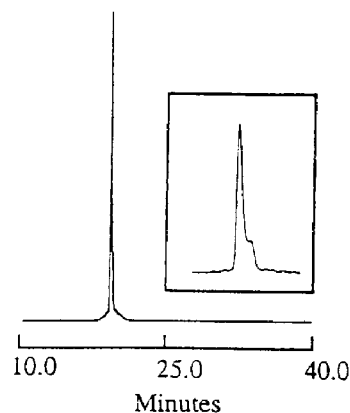
Figure 1D:
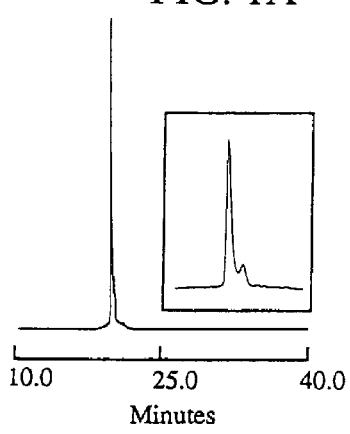
Figure 1E:
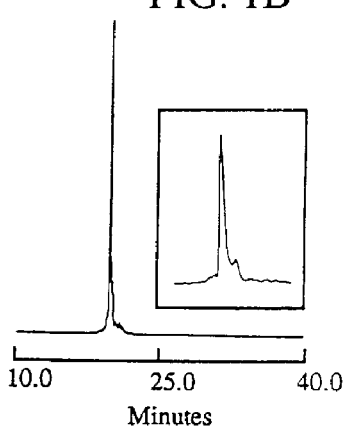
Figure 1F:
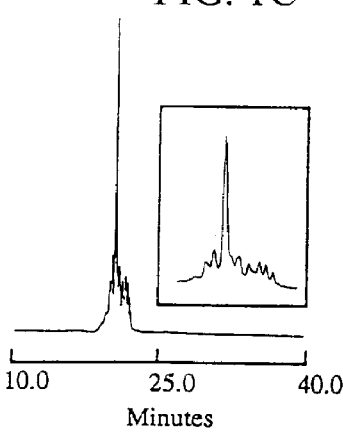

The present invention provides a new method of detritylating oligonucleotides synthesized by standard chemical techniques. The method comprises contacting a 5'-DMT oligonucleotide with the H$^+$ form of a "DOWEX," AMBERLYST" or "AMBERLITE" ion-exchange resin. These resins are strongly acidic cationic exchange materials. It has unexpectedly been found that the H$^+$ form of these ion-exchange resins detritylate 5'-DMT oligonucleotides much more rapid than prior art methods and eliminate much of the processing required by prior art methods.

The resin should be prepared before before use in the present invention. The resin should be soaked in acid (e.g., 1N HCl) (preferably for about 30 minutes) and subsequently washed with water followed by an aqueous base (e.g., 1N NaOH) solution. On the order of 10 times the resein volume of water and 2 times the resin volume of NaOH are used. Subsequent treatments with water, followed by 1N HCl and then water are repeated until the washings are at neutral pH. Other acids such as sulfuric and phosphonic acid may be used. Other bases such as NH$_4$OH, KOH, or other strong alkalis can be used in place of NaOH.

A variety of resins with different degrees of cross linking and mesh sizes are commercially available. The mesh size and degree of cross linking of this resin precludes any retention of the oligonucleotide within the resin pores. Among the resins suitable for use in the present invention are the following "DOWEX" resins: 50WX2-100, 50WX2-200, 50WX2-400, 50WX4-200, 50WX4-400, 50WX8-100, 50WX8-200, 50WX8-400, all of which are commercially available from, for example, Aldrich (Milwaukee, Wis.). Other suitable resins include "AMBERLYST 15," "AMBERLITE IR-120," the H$^+$ form of "AMBERLITE 200," the H$^+$ form of "AMBERLITE IR-200 C," and "AMBERLITE IRC-50," all of which are available from Fluka (Ronkonkoma N.Y.). These resins are reported to have meshes in the range of about 16 to about 400 and cross-linking in the range of from about 2% to about 8%. In general, any resin having the characteristics of the foregoing resins can be used in the present invention. In a preferred embodiment of the present invention the H$^+$ form of "DOWEX" 50WX-2-200 ion-exchange resin (2% cross-linking, 100–200 dry mesh) is used.

5'-DMT-oligonucleotides are detritylated by loading them onto a chromatography column packed with previously prepared resin. Water is then added to the column to elute the oligonucleotide. Reaction time can vary from as little as 5 min. to as long as 2 hours for complete detritylation without significant loss of oligonucleotide product. Shorter times can of course be used. Longer reaction times may also be used, but the longer the reaction time the greater the likelihood of loss of product due to, for example, depurination. We have found that successful detritylation can be accomplished by reaction with the resin for up to 2 hours. Some loss of oligonucleotide is observed after reaction for 12 hours. Varying degrees of decomposition will be observed for reaction times of more than 2 hours. In any case, detritylation with acetic acid would take longer. The skilled artisan can easily determine the appropriate detritylation time for a particular application based upon the factors disclosed herein and upon the amount of time, percentage of detritylation, and amount of oligonucleotide loss that is acceptable for that application.

The method of the present invention can be used on any oligonucleotide bearing a 5'-DMT moiety. Although the method can be used successfully on any oligonucleotide sample size, it is particularly advantageous when used to detritylate large batches of oligonucleotides resulting from large scale synthesis (e.g., ca. ≧10 μmol).

Typically, the present method is used to detritylate 5'-DMT oligonucleotides chemically synthesized by any standard technique (e.g., the phosphoramidite method) that uses (or can use) DMT as a 5' protecting group. Such oligonucleotides are generally synthesized on a solid support (e.g., CPG) from which they must be cleaved, but the present invention can also be applied to oligonucleotides synthesized in the solution phase. Following cleavage from the solid support, the base and phosphate protecting groups are optionally removed and the DMT-on oligonucleotide subject to preparative HPLC.

The present invention offers a variety of advantages over the prior art methods of detritylation, particularly the use of acetic acid. Complete detritylation is observed in as little as 5–10 minutes as compared to the typical time of 2 hours required when using acetic acid. Furthermore, upon detritylation the resin retains the released DMT species, thereby eliminating the extraction step associated with acetic acid detritylation. Not only does this result in further time savings, it also reduces the loss of expensive oligonucleotide that occurs during extraction. Importantly, no side reactions, such as depurination, occur when detritylation by the present method is restricted to 2 hours or less. Importantly, the present method is also easy and convenient to use. In addition, the resin can be processed and re-used, resulting in additional cost savings.

The following examples are provided for illustrative purposes only and are not intended, nor should they be construed, as limiting the invention in any manner.

EXAMPLES

As used herein, all chemicals, reagents and solvents, were DNA-synthesis grade and purchased from their respective manufacturers and used as such. Detritylation experiments were performed using "DOWEX" 50WX-2-200 ion-exchange resin (2% cross-linking, 100–200 dry mesh) (Aldrich, Milwaukee, Wis.). DMT-T-CPG was prepared according to the general protocol as described in *Methods in Molecular Biology*, Vol. 20, supra, for example. Preparative HPLC was done using Waters 650E unit equipped with a Rainin UV detector (Rainin Instruments, Woburn, Mass.). Analytical HPLC was done using a Waters 650E unit (Waters, Milford, Mass.) equipped with a 996 Photodiode Array Detector. Polyacrylamide gel electrophoresis (PAGE) and capillary gel electrophoresis (CE) were carried out as described in Iyer et al., *Nucleosides & Nucleotides*, supra.

Synthesis of Oligonucleotides

Oligonucleotides SEQ ID NOs 1–3 having the sequences displayed in Table 1 were synthesized on a 10 μmol scale (DMT-on) using a Biosearch 8700 DNA synthesizer (Biosearch, Milford, Mass.) as reported in Iyer et al., *Bioorg. Chem.* 23, 1 (1995). Following synthesis, the CPG-bound oligonucleotide was treated with 28% NH$_4$OH (55 °C., 8 h) to completely cleave the oligonucleotide from the support and remove the base and phosphate protecting groups. The ammonia solution was concentrated to dryness in vacuo to obtain the crude oligonucleotide, which was purified as described below.

TABLE 1

| SEQ ID NO | SEQUENCE |
|---|---|
| 1 | 5'-CTCTCGCACCCATCTCTCTCCTTCT-3'[a] |
| 2 | 5'-CUCUCGCACCCATCTCTCTCCUUCU-3'[b] |
| 3 | 5'-AGCTGCTACTAGTAGCTCGACATGT-3'[c] |

[a]All internucleotide linkages are phosphorothioates.
[b]Underlined nucleotides are 2'-O-methyl phosphorothioates; all others are phosphorothioates.
[c]All internucleotide linkages are phosphodiester linkages.

HPLC Purification and Analysis of Oligonucleotides

The crude oligonucleotides were purified by preparative HPLC on a C$_{18}$ reverse phase column (15 mm×300 mm). The mobile phase consisted of buffer A (0.1M NH$_4$OAc) and buffer B (0.1M NH$_4$OAc:CH$_3$CN, 20:80). Elution was carried out at a flow rate of 12 ml/min, using the following gradient: 0–2 min of 100% of buffer A followed by 2–50 min. of 100%–50% of buffer B. Analytical HPLC was performed using the same mobile phase and gradient as above at a flow rate of 1.5 ml/min on a microsorb MV C$_{18}$ column (4.6 mm×250 mm) (Rainin Instruments, Woburn, Mass.).

Assay for Dimethoxytrityl Residue in Oligonucleotides

The detritylated oligonucleotide solution (20 A$_{260}$ units) was lyophilized. The residue was suspended in 3 ml of acetonitrile, and 1 ml of HClO$_4$/ethanol (60:40) was added to the mixture. After vigorously shaking, the mixture was centrifuged and the absorbance of the supernatant at $\lambda_{495}$ was determined. $^{32}$P-labeling of Oligonucleotides and PAGE Analysis 2 units of polynucleotide kinase (New England Biolabs, Beverly, Mass.), 2 μl of 10×kinase buffer, 0.01 μCi of [γ$^{32}$P-ATP] (6 Ci/mmol, Amersham Corp., Arlington Heights, Ill.) and water (to adjust the total volume to 20 μl) were added to 6 pmoles of oligonucleotide. The mixture was incubated at 37° C. for 1 hour, subjected to PAGE and autoradiography as described in Iyer et al., *Nucleosides & Nucleotides*, supra, and Iyer et al., *Bioorg. Chem.*, supra.

Example 1

Detritylation of Oligonucleotides Using Acetic Acid 4 ml of glacial acetic acid was added to 1 ml of 50 A$_{260}$ units of HPLC purified oligonucleotide. The mixture was kept at room temperature for one hour and then was concentrated to dryness in vacuo. The residue was dissolved in 10 ml of water and a small portion of it used for HPLC analysis, measurement of dimethoxytrityl residue, and $^{32}$P-labeling. The remaining solution was loaded on a Sephadex G-25 column, and the desalted solution thus obtained was lyophilized to dryness to obtain pure oligonucleotide.

Example 2

Detritylation of Oligonucleotides Using "DOWEX" Resin

Prior to use in detritylation, the resin was soaked in 1N HCl for 30 minutes, washed with water and followed by washing with 1N NaOH solution. The resin was again washed with water, 1N HCl, and finally with water until the washings were at neutral pH. The wet resin was used for detritylation of oligonucleotide as follows: 1 ml of 50 A$_{260}$ units of HPLC-purified oligonucleotide was loaded onto 1 g (dry weight, 7 ml, wet volume) of the resin (column size 1×15 cm). Ten minutes after loading, water (10 ml) was added to the column and the oligonucleotide eluted. A small portion of the eluted oligonucleotide solution was used for HPLC analysis, dimethoxytrityl cation assay and $^{32}$P labeling. The remaining solution was evaporated to dryness in vacuo and passed through a Sephadex G-50 column for desalting. The desalted solution was lyophilized to dryness to obtain the pure oligonucleotide.

Example 3

Comparison of Detritylation of Pyrimidine-Rich Oligonucleotides by Acetic Acid and "DOWEX"

In order to systematically evaluate the potential of the "DOWEX" resin as a detritylation reagent, we first prepared two pyrimidine-rich (~80% C-T) 25-mer oligodeoxyribonucleoside phosphorothioates SEQ ID NOs 1 and 2 ("DMT-on") on a 10 μmol scale using standard phosphoramidite chemistry. Following usual deprotection and HPLC purification, the DMT-on oligonucleotides SEQ ID NOs 1 and 2 were detritylated both by standard acetic acid protocol (80% acetic acid) described in Example 1 and with "DOWEX" resin (10 min exposure) as described in Example 2. Subsequent processing (Padmapriya et al., supra) afforded pure oligonucleotides. The yield of oligonucleotides obtained using the resin was slightly better (on the order of 10%) than using acetic acid, likely due to losses during extractive processing required by the acetic acid approach. Comparative analysis by HPLC and capillary gel electrophoresis (CE) of the oligonucleotides obtained using both protocols showed them to be identical to one another.

Example 4

Detritylation of Purine-Rich Oligonucleotides by Acetic Acid and "DOWEX"

To demonstrate that purine-rich oligonucleotides can be processed in a similar manner and to ascertain the time course of detritylation, the phosphoric diester oligonucleotide SEQ ID NO 3 was synthesized on a 10 μmol scale. The HPLC-purified SEQ ID NO 3 (DMT-on) (500 A$_{260}$ units) was divided into 10 portions. Detritylation reaction of the oligonucleotide was done by using either 80% acetic acid or by passing through a column packed with "DOWEX 50 WX" resin. The time course of detritylation was monitored by HPLC analysis. FIG. 1 displays some of the results. Comparing panel A of FIG. 1 (DMT-on SEQ ID NO 3) with panel B (after reaction with the Na$^+$ form of the resin) shows that the Na$^+$ form of the resin results in only a small amount of detritylation. Panels C-F demonstrate that the HPLC profiles of SEQ ID NO 3 detritylated with for 1 hour with 80% acetic acid (panel C) and with the H$^+$ form of the resin for 10 min. (panel D), and 2 h (panel E) are virtually identical. Detritylation with acetic acid required about one hour to effect complete detritylation. By contrast, detritylation of SEQ ID NO 3 was virtually complete when the oligodeoxynucleotide had been exposed to the resin for only 10 minutes. Panel F shows that some loss of oligonucleotide is observed when it is allowed to react in the "DOWEX" column for 12 hours.

Table 2 displays the time course of detritylation of 5'-O-DMT 3 with the H$^+$ form of the "DOWEX" resin determined as a measure of DMT-ol (i.e., the alcohol form of DMT) content in the oligonucleotide. At different time-points, 20 $A_{260}$ units of DMT-on SEQ ID NO 3 that had been exposed to the resin was removed, frozen and lyophilized dry. The residue was suspended in 3 ml of acetonitrile and 1 ml of $HClO_4$/ethanol (60:40) was added. After shaking, the mixture was centrifuged and assayed for DMT residue in the oligonucleotide and the total absorbance of the supernatant at $\lambda_{495}$ was determined.

TABLE 2

| Table (min) | $A_{495}$ units |
|---|---|
| 0 | 5.80 |
| 2 | 0.45 |
| 10 | 0.02 |
| 30 | 0.02 |
| 120 | 0.01 |
| 720 | 0.01 |

Furthermore, exposure to the resin for up to 2 hours did not result in any noticeable degradation (as evaluated by HPLC and PAGE, vide infra). Degradation (likely resulting from depurination) was apparent only if the oligonucleotide was exposed to the resin for 12 hours or longer.

In both this Example and Example 3, the liberated 4,4'-dimethoxytrityl species remained bonded to the resin during detritylation by the resin (as revealed by the formation of orange-red colored resin) and did not elute out along with the oligonucleotide. This observation was confirmed by the results of the "DMT assay" presented in Table 2, which showed the absence of any DMT species in the oligonucleotide. In addition, the partial desalting occurred when the $NH_4^+$ ions (present as $N_4H$ OAc in the HPLC-purified oligonucleotide) exchanged with $H^+$ of the resin to liberate acetic acid, thereby facilitating further processing of the oligonucleotide. Although the pH of the solution containing the oligonucleotide was ca. 4-5, our studies show that detritylation of the oligonucleotide had already occurred when it came in contact with the resin and not after its passage through it. This is confirmed by a control experiment performed using the $Na^+$ form of "DOWEX," in which detritylation of the oligonucleotide was not observed. (FIG. 1B) After use for detritylation, the $H^+$ "DOWEX" resin could be regenerated by washing with 1N HCl and water.

Following detritylation, the solution containing the oligonucleotide was concentrated and desalted by passing it through a Sephadex G-25 column. Desalting could be done directly without the need for the additional extractive workup that is usually required with the acetic acid protocol.

Example 5

Figure 2:
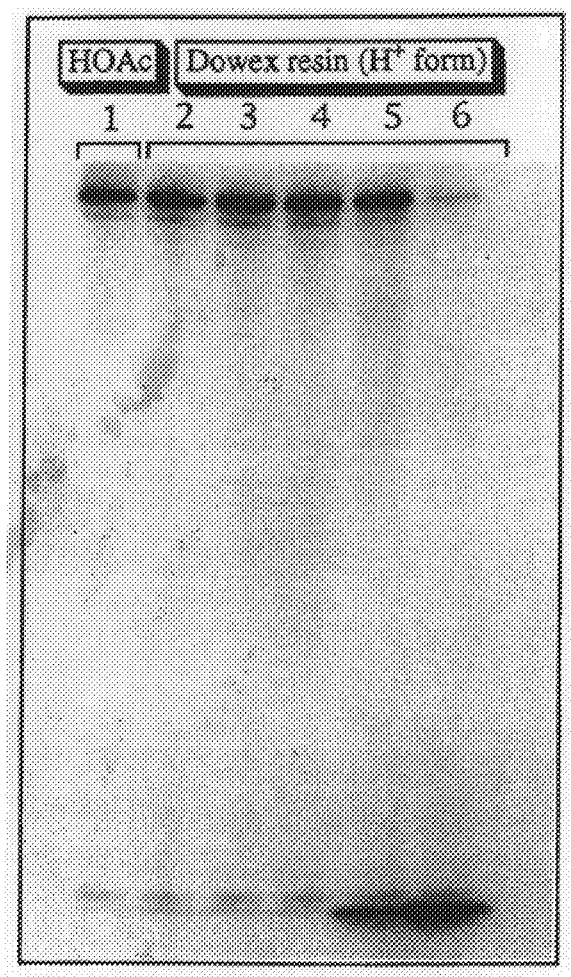
FIG. 2 displays an autoradiogram of 5'-$^{32}$P-labeled SEQ ID NO 3 prepared after detritylation of DMT-on SEQ ID NO 3 with acetic acid and "DOWEX" as a function of detritylation time. Lane 1 is 1 hour of detritylation with acetic acid. Lanes 2–6 are after 2 min., 10 min., 30 min., 2 hours, and 12 hours, respectively, detritylation with "DOWEX" resin.

Biological Equivalence of "DOWEX" Detritylated and Acetic Acid Detritylated Oligonucleotides Samples of SEQ ID NO 3 that had been obtained by detritylation with acetic acid and with the "DOWEX" resin for different time periods were $^{32}P$-labeled at the 5'-end using T4 polynucleotide kinase and [$\gamma$-$^{32}P$]ATP and analyzed by PAGE (20%) followed by autoradiography. (FIG. 2) In case of the oligonucleotides that were obtained following detritylation using the resin, no depurination or other damage was observed for oligonucleotides that had remained in contact with the resin for up to 2 hours, and these oligonucleotides appeared identical to that detritylated with 80% acetic acid. Samples obtained after prolonged exposure (up to 12 h) to the resin, however, did not label efficiently (as estimated by the intensity of the 25-mer band), presumably because it had suffered degradation by depurination. This result was earlier revealed by HPLC analysis. (FIG. 1)

We claim:

1. A method of detritylating a 5'-DMT oligonucleotide comprising contacting the oligonucleotide with one or more strongly acidic cationic exchange resins in the hydrogen form selected from the group consisting of the "DOWEX" resins 50WX2-100, 50WX2-200, 50WX2-400, 50WX4-200, 50WX4-400, 50WX8-100, 50WX8-200, 50WX8-400 and the resins "AMBERLYST 15," "AMBERLITE IR-120," "AMBERLITE 200," "AMBERLITE 200," and "AMBERLITE IRC-50", wherein the resins are in the H⁺ form.

2. The method of claim 1 wherein said contacting is conducted for at least about 5 minutes.

3. The method of claim 1 wherein said contacting is conducted from about 5 minutes to about 2 hours.

4. The method of claim 1 where said contacting is conducted for about 10 minutes.

5. The method of claim 1, wherein the resin is "DOWEX" 50WX2-200.

6. The method of claim 5 wherein said contacting is conducted for at least about 5 minutes.

7. The method of claim 5 wherein said contacting is conducted from about 5 minutes to about 2 hours.

8. The method of claim 5 where said contacting is conducted for about 10 minutes.

* * * * *